(12) United States Patent
Bechtold et al.

(10) Patent No.: US 11,771,384 B2
(45) Date of Patent: Oct. 3, 2023

(54) POSITIONING OF AN EXAMINATION OBJECT IN RELATION TO AN X-RAY DEVICE

(71) Applicant: Siemens Healthcare GmbH, Erlangen (DE)

(72) Inventors: Mario Bechtold, Hemhofen (DE); Daniela Bolte, Borchen (DE); Anja Brundobler, Neunkirchen Am Brand (DE); Helmut Gollwitzer, Erbendorf (DE); Anna Jerebko, Paoli, PA (US); Wolfgang Neuber, Pressath (DE); Marcus Radicke, Veitsbronn (DE); Karin Ratzmer, Hilpoltstein-Meckenhausen (DE); Juliane Ritter, Erlangen (DE); Ann-Christin Roessler, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 1286 days.

(21) Appl. No.: 16/234,840

(22) Filed: Dec. 28, 2018

(65) Prior Publication Data
US 2019/0209106 A1 Jul. 11, 2019

(30) Foreign Application Priority Data
Jan. 5, 2018 (DE) .......................... 102018200108.1

(51) Int. Cl.
*A61B 6/12* (2006.01)
*A61B 6/08* (2006.01)
(Continued)

(52) U.S. Cl.
CPC .............. *A61B 6/12* (2013.01); *A61B 6/0414* (2013.01); *A61B 6/06* (2013.01); *A61B 6/08* (2013.01);
(Continued)

(58) Field of Classification Search
CPC ........... A61B 6/0414; A61B 6/06; A61B 6/08; A61B 6/12; A61B 6/462; A61B 6/502; A61B 6/54; A61B 6/588
See application file for complete search history.

(56) References Cited

U.S. PATENT DOCUMENTS

2005/0063509 A1* 3/2005 Defreitas ............... A61B 6/585 378/37
2005/0226375 A1* 10/2005 Eberhard ............... A61B 6/584 378/62

(Continued)

OTHER PUBLICATIONS

German Office Action Published Jul. 27, 2018.

*Primary Examiner* — Amelie R Davis
(74) *Attorney, Agent, or Firm* — Harness, Dickey & Pierce, P.L.C.

(57) ABSTRACT

A system and a method are respectively for positioning an examination object and evaluation of an image with respect to a positioning of a breast of an examination object in relation to an x-ray device. In an embodiment, the system includes an x-ray device including at least one compression device to fix a breast of the examination object; at least one camera, arranged in relation to the x-ray device such that images are acquirable via the at least one camera, the images showing a current positioning of the breast of the examination object in relation to the x-ray device; and at least one display device, embodied to display the images.

22 Claims, 4 Drawing Sheets

(51) Int. Cl.
*G06T 7/62* (2017.01)
*A61B 6/04* (2006.01)
*A61B 6/06* (2006.01)
*A61B 6/00* (2006.01)
*G06T 7/00* (2017.01)
*A61B 5/103* (2006.01)
*A61B 5/107* (2006.01)

(52) U.S. Cl.
CPC .............. *A61B 6/462* (2013.01); *A61B 6/502* (2013.01); *A61B 6/54* (2013.01); *A61B 6/588* (2013.01); *G06T 7/0012* (2013.01); *G06T 7/62* (2017.01); *A61B 5/103* (2013.01); *A61B 5/1077* (2013.01); *G06T 2207/10028* (2013.01); *G06T 2207/10048* (2013.01); *G06T 2207/10116* (2013.01); *G06T 2207/20081* (2013.01); *G06T 2207/30068* (2013.01)

(56) References Cited

U.S. PATENT DOCUMENTS

| | | | |
|---|---|---|---|
| 2006/0071135 A1* | 4/2006 | Trovato | A61B 34/20 248/289.11 |
| 2007/0248210 A1* | 10/2007 | Selse | G06T 7/0012 382/132 |
| 2008/0087830 A1 | 4/2008 | Kashiwagi | |
| 2008/0122936 A1* | 5/2008 | Lomnes | H04N 5/2251 348/E5.025 |
| 2009/0003519 A1* | 1/2009 | Defreitas | A61B 6/025 378/37 |
| 2009/0326369 A1* | 12/2009 | Schmidt | A61B 5/064 600/424 |
| 2010/0054402 A1 | 3/2010 | Fischer et al. | |
| 2010/0054557 A1* | 3/2010 | Morita | G06V 10/24 382/128 |
| 2010/0067648 A1* | 3/2010 | Kojima | A61B 6/502 378/11 |
| 2010/0208037 A1 | 8/2010 | Sendai | |
| 2014/0336502 A1* | 11/2014 | Neelakanta | A61B 10/02 600/473 |
| 2015/0272520 A1* | 10/2015 | Kobayashi | A61B 6/06 378/62 |
| 2016/0270751 A1 | 9/2016 | Laukkanen et al. | |
| 2017/0367671 A1* | 12/2017 | Arai | A61B 6/502 |
| 2018/0116612 A1* | 5/2018 | Sakuragi | A61B 90/17 |
| 2018/0184999 A1* | 7/2018 | Davis | A61B 8/403 |
| 2019/0287241 A1* | 9/2019 | Hill | A61B 6/5282 |

* cited by examiner

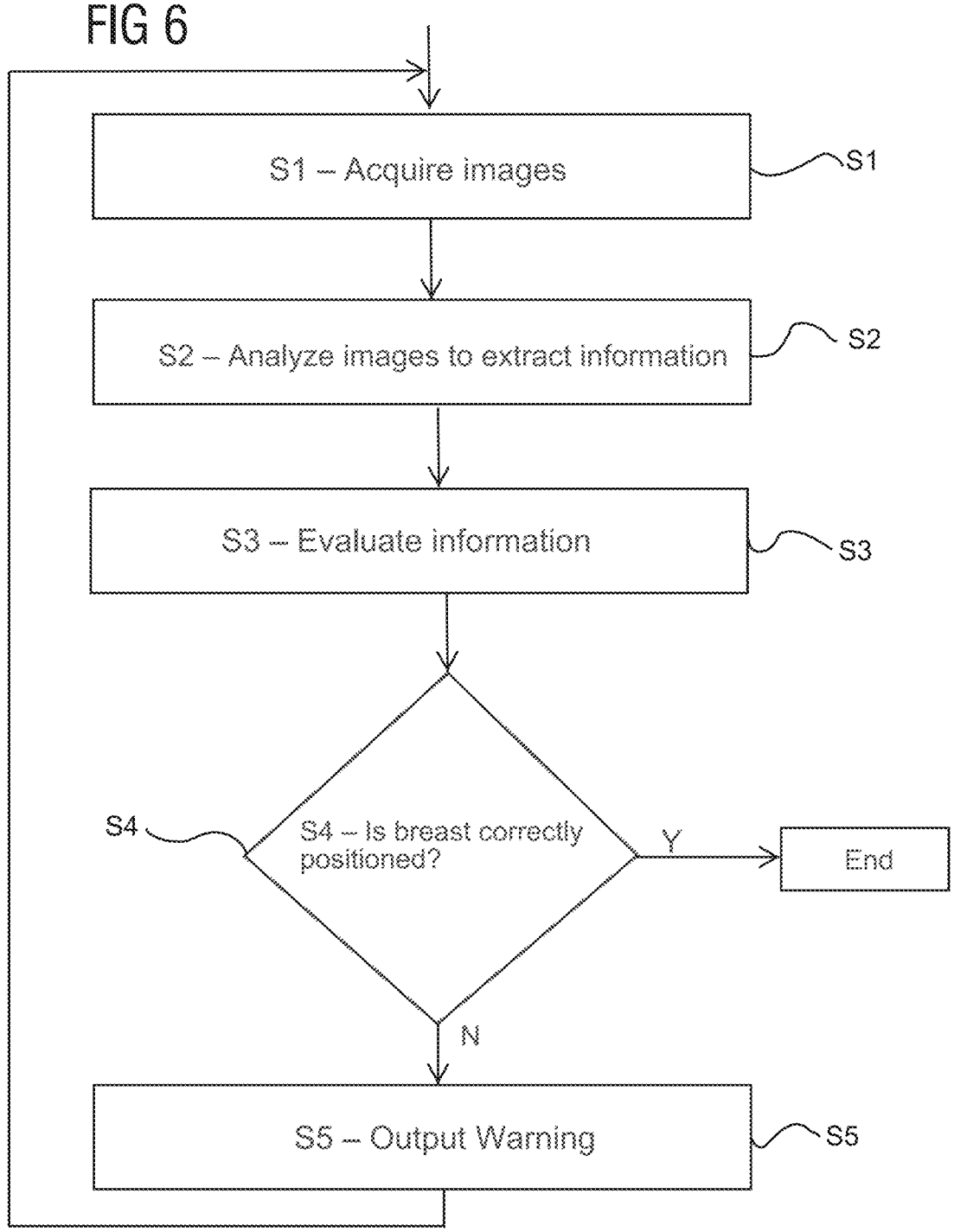

POSITIONING OF AN EXAMINATION OBJECT IN RELATION TO AN X-RAY DEVICE

PRIORITY STATEMENT

The present application hereby claims priority under 35 U.S.C. § 119 to German patent application number DE 10 2018 200 108.1 filed Jan. 5, 2018, the entire contents of which are hereby incorporated herein by reference.

FIELD

Embodiments of the invention generally relate to the positioning of an examination object, in particular of a female patient during mammography, in relation to an x-ray device.

BACKGROUND

Breast cancer screening and breast cancer diagnostics are two standard methods in medical imaging. In these methods it sometimes occurs that, during the positioning of the patient by the MTRA (medical technology radiology assistant) the patient is sometimes incorrectly positioned in relation to the x-ray device or the positioning takes longer, since, because of the arrangement of x-ray device and patient, the MTRA only has a restricted view. Therefore the result of the positioning can only be checked with difficulty. This means that the question of whether the patient's breast is fixed correctly on the x-ray detector cannot always be answered satisfactorily by the assistant during the positioning. This leads to a non-optimal workflow, since the positioning must be repeated, or in extreme cases it leads to incorrect diagnoses or to repetitions of the x-ray image recording concerned.

SUMMARY

Disclosed is a system and/or method that, in at least one embodiment, provides better support for the MTRA in the positioning of a breast of a patient relative to an x-ray detector than is the case in the prior art.

Embodiments of the invention provide a system for positioning an examination object, a method for evaluating an image in respect of a positioning of a breast of an examination object in relation to an x-ray device, a computer program product and an electronically-readable data medium. The claims define preferred and inventive forms of embodiment of the present invention.

Within the framework of at least one embodiment of the present invention, a system for positioning of an examination object in relation to an x-ray device is provided. In at least one embodiment of the invention, the system comprises the x-ray device, at least one camera and at least one display device(s) (for example one or more screens). The x-ray device comprises (in particular transparent) compression device(s) for fixing a breast of the examination object relative to the x-ray device. The camera or the number of cameras are arranged relative to the x-ray device such that images, which represent a respective current positioning of the breast of the examination object relative to the x-ray device, are able to be acquired via the at least one camera. The display device(s) are designed to present these images to an assistant undertaking the positioning of the examination object.

Within the framework of at least one embodiment of the present invention, a method for evaluation of one or more images in relation to a positioning of a breast of an examination object relative to an x-ray device is also provided. At least one embodiment of the inventive method comprises:

Acquisition of one image or of a number of images, which show a positioning of the examination object and of the breast of the examination object in relation to the x-ray device. These images are acquired in accordance with the invention so that, on the basis of these images, the location (i.e. position and orientation) of the examination object in relation to the x-ray device and also the position and/or location of the breast in relation to the x-ray device, in particular in relation to the x-ray detector of the x-ray device, can be determined.

Analysis of the image or of the images, in order, on the basis of this analysis, automatically to determine information from the image. In this step the image or the images will be evaluated, in order in particular to determine the location of the examination object relative to the x-ray device and on the other hand the position or location of the breast relative to the x-ray detector; and Automatic determination depending on the information as to whether the breast is arranged correctly relative to the x-ray detector, so that in this correct position of the breast relative to the x-ray detector, an informative x-ray recording can be created with the x-ray device. In this step it is accordingly decided whether the breast is correctly positioned or whether there is an incorrect positioning of the breast, so that the breast is to be positioned differently in relation to the x-ray detector.

Advantageously, at least one embodiment of the inventive method for evaluation of an image in respect of a positioning of a breast of an examination object in relation to an x-ray device, can work with machine learning methods or be improved with these methods. To this end the images, which show a positioning of the examination object and of the breast in relation to the x-ray device, can be assessed by a person skilled in the art as to whether or not the breast is correctly placed in relation to the x-ray device in the respective image. This assessment by the person skilled in the art is acquired automatically for each of the images, in order for example to train a neural network on the basis of these images and the respective assessment. This trained neural network can then be used to analyze an image, which shows a current positioning of the examination object and of the breast in relation to the x-ray device, in accordance with at least one embodiment of the invention and to determine on the basis of this image whether the breast is placed correctly in relation to the x-ray device.

Furthermore, at least one embodiment of the present invention describes a computer program product, in particular software, which can be loaded into a memory of a programmable control device or a processing unit of at least one embodiment of an inventive system for positioning of an examination object. With this computer program product all or different forms of embodiment of the inventive method previously described can be carried out when the computer program product is running in the control device. In this case, the computer program product may need program segments/modules, e.g. libraries and auxiliary functions, in order to realize the corresponding forms of embodiment of the method. In other words software is to be protected by a claim directed to the computer program product, with which one of the forms of embodiment of the inventive method described above can be carried out or which carries out this form of embodiment. In this case the software can involve source code (e.g. C++), which still has to be compiled and linked or which only has to be interpreted, or can involve executable software code, which only has to be loaded into the corresponding processing unit or control device for execution.

Furthermore, at least one embodiment of the present invention discloses an electronically-readable data medium, e.g. a DVD, a magnetic tape, a hard disk or a USB stick, on which electronically-readable control information, in particular software (cf. above), is stored. When this control information (software) is read from the data medium and stored in a control device or processing unit of an inventive system for positioning of an examination object, all inventive forms of embodiment of the method previously described can be carried out.

Furthermore, at least one embodiment of the present invention discloses a system for positioning of an examination object, comprising:

an x-ray device including at least one compression device to fix a breast of the examination object;

at least one camera, arranged in relation to the x-ray device such that images are acquirable via the at least one camera, the images showing a current positioning of the breast of the examination object in relation to the x-ray device; and at least one display device, embodied to display the images.

Furthermore, at least one embodiment of the present invention discloses a method for evaluation of an image with respect to a positioning of a breast of an examination object in relation to an x-ray device, the method comprising:

acquiring at least one image, the at least one image showing a positioning of the examination object in relation to the x-ray device and a positioning of the breast in relation to the x-ray device;

analyzing the at least one image acquired, to extract information from the at least one image; and determining, depending on the information extracted, whether or not the breast is placed correctly in relation to the x-ray device, to create an informative x-ray image of the breast with the x-ray device upon the examination object and the breast being located in a correct positioning, acquired via the at least one image showing the positioning of the examination object in relation to the x-ray device and the positioning of the breast in relation to the x-ray device.

BRIEF DESCRIPTION OF THE DRAWINGS

The present invention will be described in detail below on the basis of inventive forms of embodiment with reference to the figures.

FIG. 6 shows the flowchart of an embodiment of an inventive method for evaluation of an image in respect of a positioning of a breast in relation to an x-ray device.

DETAILED DESCRIPTION OF THE EXAMPLE EMBODIMENTS

Figure 1:
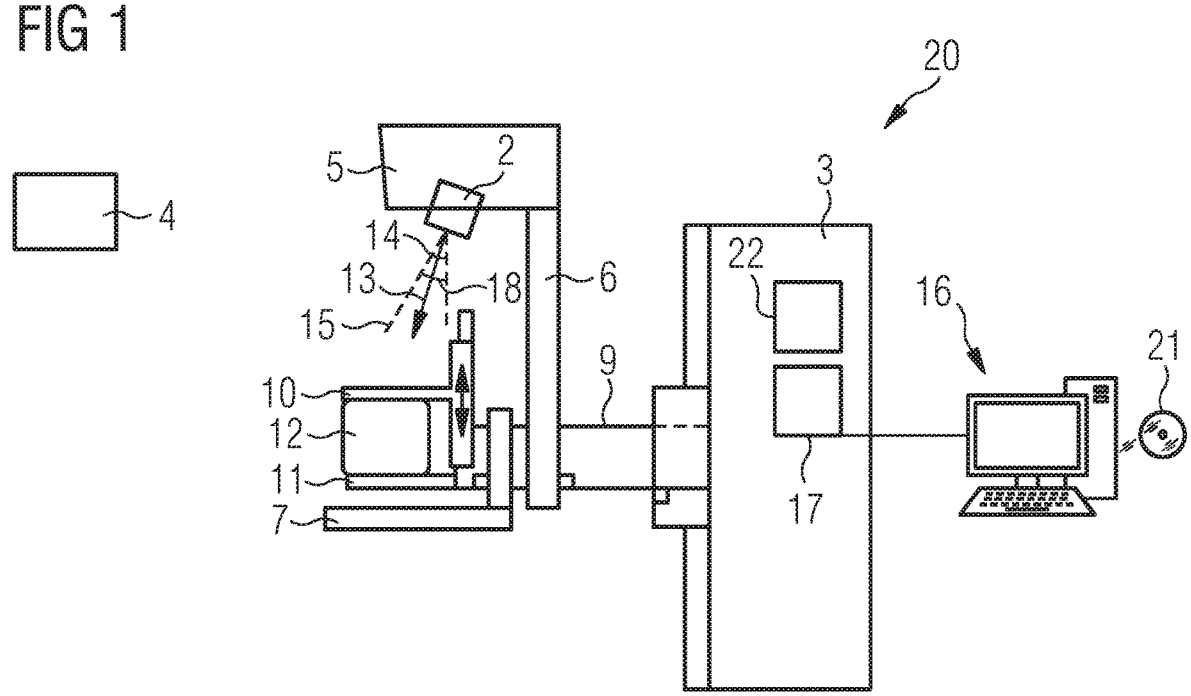
FIG. 1 shows an embodiment of an inventive system schematically.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group)

that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Most of the aforementioned components, in particular the identification unit, can be implemented in full or in part in the form of software modules in a processor of a suitable control device or of a processing system. An implementation largely in software has the advantage that even control devices and/or processing systems already in use can be easily upgraded by a software update in order to work in the manner according to at least one embodiment of the invention.

Within the framework of at least one embodiment of the present invention, a system for positioning of an examination object in relation to an x-ray device is provided. In at least one embodiment of the invention, the system comprises the x-ray device, at least one camera and at least one display device(s) (for example one or more screens). The x-ray device comprises (in particular transparent) compression device(s) for fixing a breast of the examination object relative to the x-ray device. The camera or the number of cameras are arranged relative to the x-ray device such that images, which represent a respective current positioning of the breast of the examination object relative to the x-ray device, are able to be acquired via the at least one camera. The display device(s) are designed to present these images to an assistant undertaking the positioning of the examination object.

On the basis of the images displayed on the display device(s), which show the breast relative to the x-ray device, or more precisely to the x-ray detector, the MTRA is in a position at all times to check the positioning result (i.e. the current positioning of the breast in relation to the x-ray detector). Therefore the MTRA can advantageously intervene immediately and correct the positioning of the breast in relation to the x-ray detector, when the positioning result shown on the display device(s) is not satisfactory.

In this case the at least one camera can be attached to a housing of a collimator of the x-ray device or to a housing of a tube head of the x-ray device.

The fastening of the at least one camera to the housing of the collimator or of the tube head enables the at least one camera to acquire images of the breast from above. Therefore the positioning of the breast on the x-ray detector can advantageously be shown very well on the basis of these images.

It should be pointed out however that, in accordance with at least one embodiment of the invention, the at least one camera can also be arranged at other positions on the x-ray device or also at least partly on one side of the x-ray device.

In accordance with a preferred inventive form of embodiment, the at least one camera involves precisely one camera. This camera is arranged above the breast in the area of the collimator outside the x-ray beam of the x-ray device within an anterior/posterior plane in relation to the examination object, which runs essentially through the middle of a breast arranged on the x-ray detector. In this case a direction of image acquisition of the camera within this anterior/posterior plane lies within an angular range that is delimited by a first leg and by a second leg. The first leg runs at right angles from top to bottom (from the camera), and the second leg runs at an angle of 20° to the first leg from the top (from the camera) obliquely down towards the examination object.

By the direction of image acquisition lying within the described angular range, it is advantageously insured that the images at least partly also show the front side of the patient, whereby the distance between the patient and the x-ray detector can also be checked on the basis of the images.

In accordance with another preferred inventive form of embodiment, the at least one camera comprises precisely two cameras, whereby a stereotactic evaluation of the images of these two cameras is made possible.

The stereotactic evaluation of the images from two cameras advantageously makes it possible to acquire spatial information, which can be employed in its turn for precise evaluation of the current positioning of the breast relative to the x-ray detector.

In relation to the storage of images acquired by the at least one camera, the following options exist in accordance with embodiments of the invention:

On the one hand the images or data can be transmitted without an intermediate step (i.e. without being stored) from the camera to the display device(s) effectively as a live image. With this option the images will not be stored, which has advantages in respect of data protection and ethics.

On the other hand, and embodiment of the inventive system can comprise storage device(s) in order to store the images or selected images. These stored images can then be stored in an appropriate patient folder (i.e. in an area of storage assigned to the patient) for answering further diagnostic questions.

Over and above this the at least one camera can comprise a thermal imaging camera.

On the basis of the images acquired by the thermal imaging camera there can then be a better differentiation of the breast in relation to its surroundings (e.g. the x-ray detector) by comparison with a normal camera (i.e. a non-thermal imaging camera), in order ultimately to undertake a better evaluation of the positioning of the breast in relation to the x-ray device on the basis of this differentiation.

Over and above this the system can be embodied to analyze the images of the thermal imaging camera, in order, through this analysis, to establish information on the basis of the images about a subcutaneous tumor or a breast inflammation in the breast of the examination object. Since tumors have a higher blood flow than healthy tissue, tumors radiate more heat, which can be detected with the thermal imaging camera. Since the compression plate is in particular embodied from plastic, the compression plate advantageously does not represent a source of errors for the image acquired by the thermal imaging camera.

In accordance with at least one embodiment of the invention, the images of a thermal imaging camera can accordingly not only deliver better results in relation to the positioning of the breast relative to the x-ray device, but also advantageously make it possible in addition to acquire diagnostic information with which a later diagnostic evaluation of the x-ray images of the breast can be corroborated.

In accordance with a further inventive form of embodiment the display device(s) are able to be adjusted or positioned, so that, depending on a location (i.e. a position and direction of view) of an assistant, who is placing the patient in relation to the x-ray detector, they are able to be placed in the direction of view of the assistant.

This form of embodiment advantageously makes it possible for at least one monitor of the display device(s) to be set or positioned manually by the assistant themselves or automatically so that the assistant at least always has this monitor in view during the positioning of the patient and, by way of this monitor, has a direct optical check on the location of the breast of the patient in relation to the x-ray detector.

In accordance with at least one embodiment of the invention, it is also possible for the display device(s) to comprise a special headset, which is embodied such that this headset shows the images otherwise presented on the at least one monitor.

Such an inventive headset can either be used instead of or in addition to the at least one monitor. Wearing this headset indicates that the assistant, who is undertaking the positioning of the patient in relation to the x-ray detector, is advantageously in a position at all times, on the basis of the images shown by the headset, to check the positioning of the breast of the patient in relation to the x-ray detector.

In accordance with a further inventive form of embodiment the system comprises a further camera, in order to acquire (further) images of the assistant, who is placing the examination object in relation to the x-ray detector. In this case the system is in a position, by a corresponding evaluation of these further images of the further camera, to determine a current direction of view and a current position of the assistant. Depending on this current direction of view and current position of the assistant, the display device(s) (for example a monitor of the display device(s)) can then be arranged such that this display device(s) is located in the current direction of view of the assistant.

This inventive form of embodiment advantageously makes it possible, by way of the further or additional camera, to detect the location (i.e. position and direction of view) of the assistant, so that, depending on this location, it can determine the optimum position of the display device(s) and set the display device(s) automatically to this optimum position. This advantageously guarantees that the display device(s) is always located in the field of view of the assistant.

The inventive forms of embodiment described above, in which the display device(s) (for example a monitor) is placed manually or automatically, can comprise the following inventive variants:

For example the monitor can be attached to a movable carriage, which is accordingly moved manually by the assistant or automatically by the system. Specifically with this variant, but also generally with all forms of embodiment or variants, the data of the images from the at least one camera can be transmitted to the display device(s) by radio (e.g. by WLAN).

On the other hand the monitor can be attached movably to a ceiling mount, so that it can be moved manually or automatically into the desired position or location.

In accordance with a further inventive form of embodiment, the system can be embodied to analyze the images acquired with the at least one camera, in order, through this analysis, to determine a biopsy needle and a position of the biopsy needle in relation to the breast of the patient in the images.

In this form of embodiment, the at least one camera can comprise a stereo camera or a normal camera at two different positions respectively, in order to determine the location (i.e. the position and direction) of the biopsy needle in space. This means that this form of embodiment makes possible not only a recognition of the biopsy needle, but also a so-called needle checking (i.e. a precise specification of the location and dimensions of the biopsy needle in the space, in particular in relation to the breast of the patient).

In accordance with a further inventive form of embodiment, the system is embodied to analyze the images, in order, on the basis of this analysis, to determine the spatial extent of the breast to be examined. The system is further embodied in particular to adjust at least one collimator of the x-ray device as a function of the dimensions determined such that the x-rays only irradiate the breast to be examined. Over and above this the system is embodied in particular to configure the x-ray detector such that an active surface of the x-ray detector is adapted to the dimensions determined, so that the detector only evaluates the x-rays passing through the breast to be examined and does not detect or evaluate x-rays that go past the breast.

With this form of embodiment, the x-ray device is advantageously in effect adapted to the breast to be examined. In that for example the x-ray device, through the setting of the collimator or collimators, only irradiates the breast to be examined, the radiation load on the patient is advantageously reduced to a minimum.

At least one embodiment of the inventive system advantageously makes possible a simple correct positioning of a patient in relation to an x-ray device independently of the anatomy of the patient and also independently of the anatomy and of the preference (e.g. location in front of or behind the patient) of the female or male assistant.

Within the framework of at least one embodiment of the present invention, a method for evaluation of one or more images in relation to a positioning of a breast of an examination object relative to an x-ray device is also provided. At least one embodiment of the inventive method comprises:

Acquisition of one image or of a number of images, which show a positioning of the examination object and of the breast of the examination object in relation to the x-ray device. These images are acquired in accordance with the invention so that, on the basis of these images, the location (i.e. position and orientation) of the examination object in relation to the x-ray device and also the position and/or location of the breast in relation to the x-ray device, in particular in relation to the x-ray detector of the x-ray device, can be determined.

Analysis of the image or of the images, in order, on the basis of this analysis, automatically to determine information from the image. In this step the image or the images will be evaluated, in order in particular to determine the location of the examination object relative to the x-ray device and on the other hand the position or location of the breast relative to the x-ray detector;

and

Automatic determination depending on the information as to whether the breast is arranged correctly relative to the x-ray detector, so that in this correct position of the breast relative to the x-ray detector, an informative x-ray recording can be created with the x-ray device. In this step it is accordingly decided whether the breast is correctly positioned or whether there is an incorrect positioning of the breast, so that the breast is to be positioned differently in relation to the x-ray detector.

At least one embodiment of the inventive method accordingly makes possible an automatic evaluation of images detected with a camera, in order, through this evaluation, to support the positioning of a patient in relation to the x-ray device by an MTRA.

The information can comprise a distance between the examination object and the x-ray detector in this case, for instance. It is determined in this case that the breast is not placed correctly in relation to the x-ray device or the x-ray detector, when the distance detected via the information lies above a predetermined minimum distance.

With this inventive form of embodiment, the distance between the examination object or the patient and the x-ray detector is established automatically on the basis of the images acquired. When the patient is standing too far away from the x-ray detector (i.e. the distance detected is greater than the minimum distance), the patient is positioned incorrectly, which is advantageously detected automatically.

In accordance with a further inventive form of embodiment, the at least one image comprises a first image and a second image. In this case the first image is acquired at a point in time at which the breast of the patient is arranged without the use of compression device(s) of the x-ray device relative to the x-ray device. At this point the breast to be examined is in effect laid on the x-ray detector without the compression device(s) of the x-ray device touching the breast. The second image is then acquired after the first image and thus at a later point in time, at which the breast is fixed relative to the x-ray device with the compression device(s) ready for an x-ray recording of the breast with the x-ray device. The second image thus shows the position of the breast relative to the x-ray detector at a point in time at which an x-ray recording is actually created, if incorrect positioning is not detected at this time. In the analysis of the two images a surface that the breast occupies on the detector is established as information. In a similar fashion a second surface, which the breast occupies at a later point in time on the detector is established as information in the second image. Subsequently a ratio of the second surface to the first surface is calculated. If this ratio is not greater than a predetermined ratio threshold value, it is determined that the breast is incorrectly positioned. The ratio threshold value in this case is 1,1 for example, but can also assume values of 1,2 to 1,5.

This form of embodiment requires that the surface that the breast covers on the x-ray detector is enlarged by the use of the compression device(s). By this enlargement of the surface by the use of the compression device(s) being detected and checked automatically, further information for an incorrect positioning can advantageously be established.

In accordance with a further inventive form of embodiment, one of the items of information established is a distance between the upper body of the patient and a mammilla of the breast to be examined. In this form of embodiment this distance is determined once before and once after a compression of the breast with the compression device(s). If a change in the distance by the compression is not greater than a minimum dimension, it is determined that the breast is not placed correctly in relation to the x-ray device. In this case the minimum dimension can be dependent on the previously acquired dimensions of the breast to be examined.

On account of the so-called spreading-out of the breast to be examined on the x-ray detector by the assistant, the distance between the patient and the mammilla of the breast to be examined is enlarged compared to this distance before the spreading-out. By comparing the distance obtained by the spreading-out with the distance measured or determined before the compression and by a comparison of the change in this distance with the minimum dimension, it can accordingly advantageously be checked whether the spreading-out has been carried out correctly. In this case this minimum dimension can be defined as a percentage minimum dimension for example, which defines the percentage by which the distance must be increased by the compression and/or the spreading-out.

The previously described form of embodiment requires an automatic recognition of the mammilla in the at least one image. Such a mammilla recognition can also be used in an enlarged x-ray recording (MAG) or in a biopsy, in order to recognize, depending on the position of the mammilla, whether the breast is arranged correctly in relation to an examination window.

Over and above this, on the basis of the analysis of the at least one image, a specification can be extracted as information from the at least one image as to whether tissue of the examination object, which does not belong to the breast to be examined, is discovered above the breast to be examined in the respective image to be analyzed. When tissue of the examination object or of the patient not belonging to the breast is acquired above the breast to be examined with one of the images to be analyzed, it is deduced that the breast is not placed correctly in relation to the x-ray device.

This inventive form of embodiment advantageously automatically prevents the x-ray image created being in effect falsified for example with more corpulent patients, since x-rays which pass through the breast to be examined do not pass through tissue not belonging to the breast before doing so.

In a similar fashion, on the basis of the analysis of the at least one image, a specification can be extracted as information from the at least one image as to whether a part of the breast muscle of the patient is located above the x-ray detector or in an area that is irradiated by the x-rays for recording an x-ray image with the x-ray device. If it is not recognized on the basis of the analysis that a part of the breast muscle is located in the described area, it is determined that the breast is not placed correctly in relation to the x-ray device.

For a correct placement of the breast on the x-ray detector, a specific part of the breast muscle of the patient is necessarily located in the previously described area, which is irradiated by x-rays during the recording of an x-ray image. Therefore the previously described form of embodiment advantageously offers the opportunity of checking automatically whether the patient is standing close enough to the x-ray detector when the x-ray recording for examination of the breast is made.

In accordance with a further inventive form of embodiment the information, which is extracted by the analysis of the at least one image from said image, contains a specification about the compression device(s) used for fixing or positioning of the breast. If it is detected here that the compression device(s) recognized in the at least one image does not correspond with the predetermined compression device(s) (i.e. the compression device(s) intended for the examination), an incorrect positioning is occurring, so that it is determined that the breast is not placed correctly in relation to the x-ray device.

This inventive form of embodiment advantageously automatically avoids the wrong compression device(s) (e.g. so-called paddles) being used in the positioning of the breast of the patient.

Advantageously a warning will be output, if, for example, it is recognized in one of the forms of embodiment previously described, that the breast the breast is not placed correctly in relation to the x-ray device. This warning can be of an optical and/or acoustic nature.

By it not only being determined as a function of the information extracted from the at least one image whether the breast is placed correctly in relation to the x-ray device, but additionally by a warning also being output when it is recognized automatically in accordance with at least one embodiment of the invention that the breast is not placed correctly in relation to the x-ray device, it is in effect prevented that an incorrect positioning by the assistant will not be noticed. This embodiment accordingly advantageously makes to possible that an unusual positioning (i.e. incorrect positioning) of the breast relative to the x-ray device leads to an output of a warning.

Advantageously, at least one embodiment of the inventive method for evaluation of an image in respect of a positioning of a breast of an examination object in relation to an x-ray device, can work with machine learning methods or be improved with these methods. To this end the images, which show a positioning of the examination object and of the breast in relation to the x-ray device, can be assessed by a person skilled in the art as to whether or not the breast is correctly placed in relation to the x-ray device in the respective image. This assessment by the person skilled in the art is acquired automatically for each of the images, in order for example to train a neural network on the basis of these images and the respective assessment. This trained neural network can then be used to analyze an image, which shows a current positioning of the examination object and of the breast in relation to the x-ray device, in accordance with at least one embodiment of the invention and to determine on the basis of this image whether the breast is placed correctly in relation to the x-ray device.

Furthermore, at least one embodiment of the present invention describes a computer program product, in particular software, which can be loaded into a memory of a programmable control device or a processing unit of at least one embodiment of an inventive system for positioning of an examination object. With this computer program product all or different forms of embodiment of the inventive method previously described can be carried out when the computer program product is running in the control device. In this case, the computer program product may need program segments/modules, e.g. libraries and auxiliary functions, in order to realize the corresponding forms of embodiment of the method. In other words software is to be protected by a claim directed to the computer program product, with which one of the forms of embodiment of the inventive method described above can be carried out or which carries out this form of embodiment. In this case the software can involve source code (e.g. C++), which still has to be compiled and linked or which only has to be interpreted, or can involve executable software code, which only has to be loaded into the corresponding processing unit or control device for execution.

Finally, at least one embodiment of the present invention discloses an electronically-readable data medium, e.g. a DVD, a magnetic tape, a hard disk or a USB stick, on which electronically-readable control information, in particular software (cf. above), is stored. When this control information (software) is read from the data medium and stored in a control device or processing unit of an inventive system for positioning of an examination object, all inventive forms of embodiment of the method previously described can be carried out.

FIG. 1 shows a schematic of an embodiment of inventive x-ray system 20, in particular for mammograph examinations or examinations of the breast. The x-ray system 20 comprises a support arm 9, which is height-adjustable. The support arm 9 is arranged on a stand 3. Arranged on the support arm 9 are an arm 6 provided with an x-ray radiation source 5, a flat-panel detector 7 and a compression facility consisting of a compression plate 10 and a support plate 11. Also shown schematically in FIG. 1 is a female breast 12 compressed by the compression plate 10 and the support plate 11.

The x-ray system 20 is controlled via an operating facility 16 of the x-ray system 20, which is connected to a controller 17 and an image-processing unit 22 of the x-ray system 20. Specific methods (including embodiments of the inventive method) can be loaded into the controller 17 and the operating facility 16 by way of a DVD 21.

Over and above this the x-ray system 20 comprises a camera 2, which is attached to the x-ray source 5 (more precisely to the tube head of the x-ray device), and a monitor 4. The camera 2 is attached in this case such that an image acquisition facility 13 of the camera 2 lies in an anterior/posterior plane in relation to the patient, whose breast 12 is fixed in the compression device(s) 10, 11. This anterior/posterior plane essentially runs in the middle of the breast 12. The image acquisition facility 13 is directed downwards and at an angle towards the patient, so that the image acquisition facility 13 lies within an angular range 18, which is delimited by a first leg 14 and a second leg 15. In this case the first leg 14 runs within the anterior/posterior plane at right angles downwards, while the second leg 15 is directed downwards and at an angle towards the patient within the anterior/posterior plane. The angular area 18 encloses an angle of 20° for example. Shown on the monitor 4 are images, which are acquired with the camera 2. On the basis of the images shown on the monitor 4, an assistant, who is placing the breast 12 in relation to the x-ray device or more precisely in relation to the x-ray detector 7, is in a position to check the positioning of the breast 12 in relation to the x-ray device or the detector 7.

Figure 2:
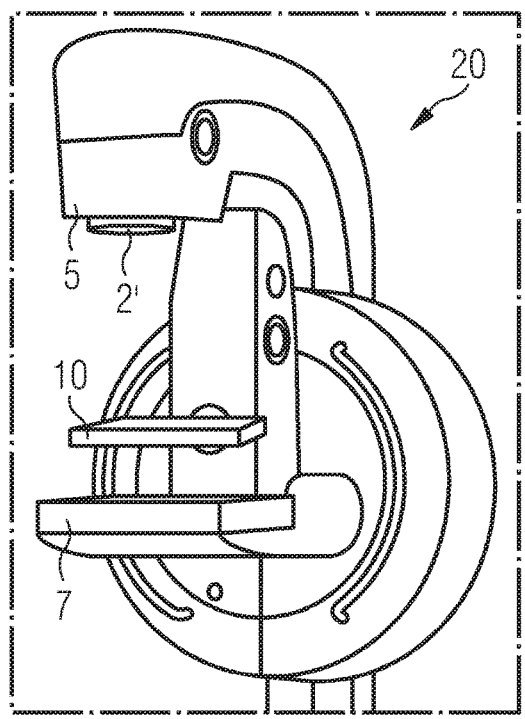
FIG. 2 shows an embodiment of a further inventive system perspectively.

In FIG. 2 shows a further embodiment of inventive x-ray system 20, this time in three dimensions. The reference number 2' shows that position on the x-ray system 20 at which the camera 2 is arranged. By contrast with the x-ray system 20 shown in FIG. 1, the x-ray system 20 shown in FIG. 2 shows only the compression plate 10 and no specific support plate 11, since the function of the support plate is effectively carried out by the detector 7.

While the x-ray system 20 of FIG. 1 is at least in principle also suitable for carrying out a tomography, during which the x-ray source 5 moves in a specific angular range around the breast 12, the x-ray system 20 of FIG. 2 is essentially suited to mammography.

Figure 3:
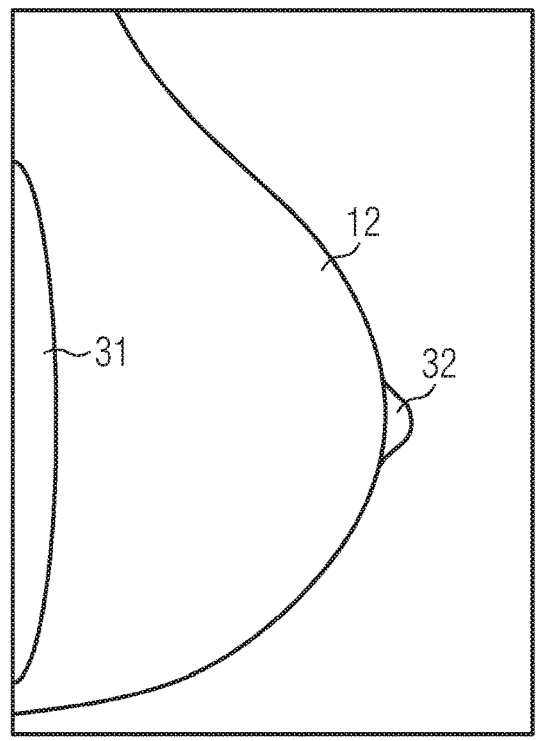
FIG. 3 shows a breast fixed to an x-ray detector schematically.

FIG. 3 shows an example of a cranio-caudal recording of a breast 12. It can be seen that the mammilla 32 and the breast muscle 31 are located at least partly in the x-ray image. To record this x-ray image shown in FIG. 3 the breast 12 has been placed correctly in relation to the x-ray device.

Figure 4:
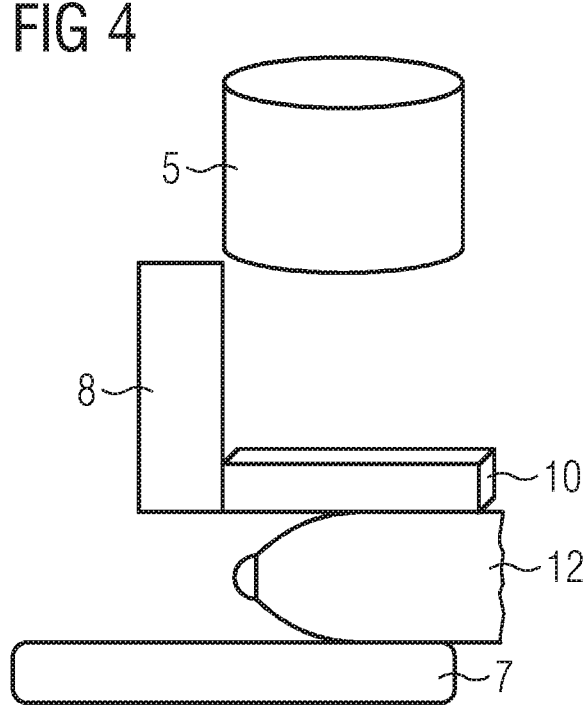
FIG. 4 also shows a breast fixed to an x-ray detector schematically.

FIG. 4 shows a breast 12 fixed in relation to an x-ray device. In this figure the breast 12 is fixed on the detector 7 in a similar manner to that shown for the x-ray system of FIG. 2 just with one compression plate 10. With a collimator 8 of the x-ray device it is insured that x-rays generated by the x-ray source 5 only irradiate the breast 12 if possible.

Figure 5:
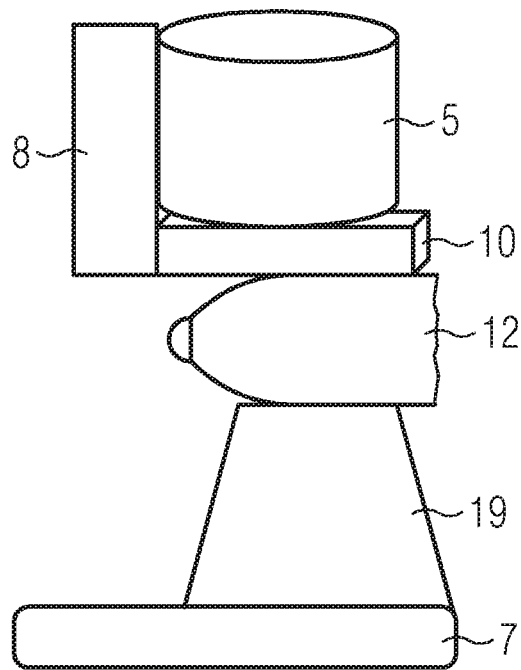
FIG. 5 shows a breast fixed in relation to the x-ray device for creating an enlarged x-ray recording.

A breast 12 fixed in relation to an x-ray device is also shown in FIG. 5. By contrast with FIG. 4, a support 19 between the breast 12 and the detector 7 is present in FIG. 5, so that the breast 12 is fixed in this case between the support 19 and the compression plate 10. The support 19 extends the distance between the breast 12 and the x-ray detector, whereby the breast 12, or at least specific areas of the breast 12, are shown enlarged on the x-ray image to be created by comparison with the configuration shown in FIG. 4.

When monitoring the positioning of the breast 12 in relation to the x-ray device, the type and the dimensions of the support 19 can also be checked automatically by a corresponding evaluation of the camera images. For example, a warning can be output automatically if it is recognized in the evaluation of the camera images that the type of the support 19 does not correspond to the predetermined type and/or that the dimensions of the support 19 do not correspond to the predetermined dimensions.

FIG. 6 shows the flowchart of an embodiment of an inventive method.

In step S1 images, which show the positioning of a breast 12 relative to an x-ray device (or more precisely to the x-ray detector 7), are acquired. For example, images can be acquired for this purpose, which are recorded by the camera 2 shown in FIG. 1. In the following step S2, the images acquired in step S1 are analyzed, in order to extract appropriate information from these images. This information can comprise a distance between the examination object and the detector 7, for example, or a specification as to whether a part of the breast muscle is located in an area that will be irradiated by x-ray radiation during the recording of the x-ray image. In step S3, this information will be evaluated, in order to determine, depending on this information, whether the breast is correctly positioned in relation to the x-ray device.

In step S4, a check is made as to whether the evaluation of the information in the preceding step S3 would lead to the result that the breast is correctly positioned. If this is the case, the method ends and an x-ray recording of the breast is produced. If, on the other hand, it is recognized in step S4 that the evaluation of the information in step S3 would lead to the result that the breast is not correctly positioned, in step S5 a corresponding warning is output. The method then returns to step S1, in which images of a renewed or corrected positioning of the breast in relation to the x-ray device are acquired. The steps S1, S2, S3 and S4 are performed until such time as the interrogation in step S4 receives a positive response, so that an x-ray recording of the breast can be produced with a correct positioning of the breast in relation to the x-ray device.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

LIST OF REFERENCE CHARACTERS

1 X-ray filter
2 Camera
2' Position of the camera
3 Stand
4 Monitor
5 X-ray source
6 Arm
7 Detector
9 Support arm
10 Compression plate
11 Support plate
12 Breast
13 Image acquisition facility
14,15 Angle legs
16 Operating facility
17 Controller
18 Angular range
19 Support
20 System
21 DVD
22 Image processing unit
31 Breast muscle
32 Mammilla
S1-S5 Method step

What is claimed is:

1. A system for positioning of an examination object, the system comprising:
an x-ray device including at least one compression device configured to fix a breast of the examination object;
at least one camera, configured to acquire at least one image showing a current positioning of the breast of the examination object in relation to the x-ray device;
processing circuitry configured to cause the system to
analyze the at least one image,
extract information from the at least one image, the information including at least one of
(i) a first distance between the examination object and a detector of the x-ray device,
(ii) a first surface where the breast covers the detector of the x-ray device in a first of the at least one image and a second surface where the breast covers the detector of the x-ray device in a second of the at least one image, the first of the at least one image acquired at a time at which the breast is being placed in relation to the x-ray device without using at least one compression device of the x-ray device and the second of the at least one image acquired at a time at which the breast is fixed in relation to the x-ray device with the at least one compression device of the x-ray device, or
(iii) a second distance between an upper body of the examination object and a mammilla of the breast,
determine whether the breast is placed correctly in relation to the x-ray device based on the information by at least one of
(i) determining that the breast is not placed correctly in relation to the x-ray device based on a comparison of the first distance to a threshold distance,
(ii) determining that the breast is not placed correctly in relation to the x-ray device in response to a ratio of the second surface to the first surface not being greater than a threshold ratio, or
(iii) determining that the breast is not placed correctly in relation to the x-ray device in response to a change in the second distance by a compression of the breast not being greater than a minimum dimension, and cause the x-ray device to generate an informative x-ray image of the breast in response to determining that the breast is placed correctly in relation to the x-ray device; and at least one display device configured to display the at least one image and a result of the determination of whether the breast is placed correctly.

2. The system of claim 1, wherein the at least one camera is attached to a housing of a collimator of the x-ray device or the at least one camera is attached to a tube head of the x-ray device.

3. The system of claim 2, wherein the at least one camera is only one camera, the one camera configured to be arranged above the breast in an area of a collimator of the x-ray device such that an image acquisition facility of the one camera lies within an anterior/posterior plane relative to the examination object in an angular range, the angular range being defined by a first leg, running at right angles from top to bottom, and a second leg, at an angle of 20° to the first leg and running obliquely from top to bottom towards the examination object wherein the area of the collimator is outside of a range of an x-ray beam of the x-ray device.

4. The system of claim 2, wherein the at least one camera includes two cameras, the two cameras configured to make a stereotactic evaluation possible.

5. The system of claim 1, wherein the at least one camera is only one camera, the one camera configured to be arranged above the breast in an area of a collimator of the x-ray device such that an image acquisition facility of the one camera lies within an anterior/posterior plane relative to the examination object in an angular range, the angular range being defined by a first leg, running at right angles from top to bottom, and a second leg, at an angle of 20° to the first leg and running obliquely from top to bottom towards the examination object, wherein the area of the collimator is outside of a range of an x-ray beam of the x-ray device.

6. The system of claim 1, wherein the at least one camera includes two cameras, the two cameras configured to make a stereotactic evaluation possible.

7. The system of claim 1, further comprising at least one storage device configured to store the at least one image.

8. The system of claim 1, wherein the at least one camera includes a thermal imaging camera.

9. The system of claim 1, wherein the at least one display device is configured to be adjusted to be placed in a direction of view of an assistant, depending on a location of the assistant.

10. The system of claim 1, wherein the at least one display device includes a headset configured to display the at least one image.

11. The system of claim 1, further comprising:

a further camera configured to acquire further images of an assistant, wherein the processing circuitry is further configured to cause the system to determine a direction of view and a position of the assistant based on the further images, and set a position of the at least one display device in the direction of view of the assistant.

12. The system of claim 1, wherein the processing circuitry is further configured to cause the system to:

analyze the at least one image to establish dimensions of the breast to be irradiated; and at least one of determine a position of a collimator of the x-ray device such that x-ray beams are restricted to the dimensions of the breast to be irradiated, or determine a position of a detector of the x-ray device such that an active surface of the detector is configured to receive x-rays passing through the dimensions of the breast to be irradiated and to not receive x-rays not passing through the dimensions of the breast to be irradiated.

13. The system of claim 1, wherein the information includes an indication indicating whether tissue of the examination object above the breast, not belonging to the breast, is established in the at least one image, and wherein the processing circuitry is further configured to cause the system to determine that the breast is not placed correctly in relation to the x-ray device in response to the indication indicating that tissue of the examination object not belonging to the breast is located above the breast.

14. The system of claim 1, wherein the information includes an indication indicating whether a part of a breast muscle of the examination object is located in an area which will be irradiated by x-rays with the x-ray device for recording of an x-ray image, and wherein the processing circuitry is further configured to cause the system to determine that the breast is not placed correctly in relation to the x-ray device in response to the indication indicating that no part of the breast muscle is located in the area.

15. The system of claim 1, wherein the information includes an indication indicating a compression device, of a plurality of compression devices, being used for positioning of the breast, and wherein the processing circuitry is further configured to cause the system to determine that the breast is not placed correctly in relation to the x-ray device in response to the compression device not matching an expected compression device.

16. The system of claim 1, wherein the processing circuitry is further configured to cause the system to output a warning in response to determining that the breast is not placed correctly in relation to the x-ray device.

17. A method for evaluation of an image with respect to a positioning of a breast of an examination object in relation to an x-ray device, the method comprising:

acquiring at least one image, the at least one image showing a positioning of the examination object in relation to the x-ray device and a positioning of the breast in relation to the x-ray device;

analyzing the at least one image;

extracting information from the at least one image, the information including at least one of (i) a first distance between the examination object and a detector of the x-ray device, (ii) a first surface where the breast covers a detector of the x-ray device in a first of the at least one image and a second surface where the breast covers the detector in a second of the at least one image, the first of the at least one image acquired at a time at which the breast is being placed in relation to the x-ray device without using at least one compression device of the x-ray device and the second of the at least one image acquired at a time at which the breast is fixed in relation to the x-ray device with the at least one compression device of the x-ray device, or (iii) a second distance between an upper body of the examination object and a mammilla of the breast;
determine whether the breast is placed correctly in relation to the x-ray device based on the information, the determining including at least one of
  (i) determining that the breast is not placed correctly in relation to the x-ray device based on a comparison of the first distance to a threshold distance,
  (ii) determining that the breast is not placed correctly in relation to the x-ray device in response to a ratio of the second surface to the first surface not being greater than a threshold ratio, or
  (iii) determining that the breast is not placed correctly in relation to the x-ray device in response to a change in the second distance by a compression of the breast not being greater than a minimum dimension; and
causing the x-ray device to generate an informative x-ray image of the breast in response to determining that the breast is placed correctly in relation to the x-ray device.

18. The method of claim 17, wherein the information includes an indication indicating whether tissue of the examination object above the breast, not belonging to the breast, is established in the at least one image, and
  wherein the determining includes determining that the breast is not placed correctly in relation to the x-ray device in response to the indication indicating that tissue of the examination object not belonging to the breast is located above the breast.

19. The method of claim 17, wherein the information includes an indication indicating whether a part of a breast muscle of the examination object is located in an area which will be irradiated by x-rays with the x-ray device for recording of an x-ray image, and
  wherein the determining includes determining that the breast is not placed correctly in relation to the x-ray device in response to the indication indicating that no part of the breast muscle is located in the area.

20. The method of claim 17, wherein the information includes an indication indicating a compression device, of a plurality of compression devices, being used for positioning of the breast, and
  wherein the determining includes determining that the breast is not placed correctly in relation to the x-ray device in response to the compression device not matching an expected compression device.

21. The method of claim 17, further comprising:
  outputting a warning in response to determining that the breast is not placed correctly in relation to the x-ray device.

22. A non-transitory computer-readable storage medium storing computer readable instructions that, when executed by one or more processors, cause a device or system to carry out the method of claim 17.

* * * * *